(12) United States Patent
Kermode et al.

(10) Patent No.: US 6,846,218 B2
(45) Date of Patent: Jan. 25, 2005

(54) BREAST STABILIZING AND POSITIONING DEVICE AND KIT

(75) Inventors: James Kermode, Los Altos, CA (US); Yumee Gang, Santa Cruz, CA (US); Charles M. Schwimmer, Los Gatos, CA (US); Tammy Gravelle, Palo Alto, CA (US); Douglas Murphy-Chutorian, Palo Alto, CA (US)

(73) Assignee: Acueity, Inc., Palo Alto, CA (US)

( * ) Notice: Subject to any disclaimer, the term of this patent is extended or adjusted under 35 U.S.C. 154(b) by 68 days.

(21) Appl. No.: 10/427,252

(22) Filed: Apr. 30, 2003

(65) Prior Publication Data

US 2004/0219864 A1 Nov. 4, 2004

(51) Int. Cl.[7] ............................. A41C 3/00; A61B 10/00
(52) U.S. Cl. ........................... 450/37; 600/562; 604/74
(58) Field of Search ............................... 450/37, 36, 1, 450/39, 51, 79, 82, 58; 2/338, 310–312; 119/852; 604/28, 73–76, 313–315, 346; 600/562, 563, 573, 576, 581

(56) References Cited

U.S. PATENT DOCUMENTS

| | | | | |
|---|---|---|---|---|
| 1,094,158 A | * | 4/1914 | Mattson | 604/388 |
| 6,004,186 A | * | 12/1999 | Penny | 450/36 |
| 6,027,396 A | * | 2/2000 | Yonchar | 450/36 |
| 6,213,840 B1 | * | 4/2001 | Han | 450/36 |
| 6,227,936 B1 | * | 5/2001 | Mendoza | 450/36 |
| 6,676,610 B2 | * | 1/2004 | Morton et al. | 600/573 |
| 6,689,070 B2 | * | 2/2004 | Hung et al. | 600/562 |
| 6,699,213 B1 | * | 3/2004 | Annis et al. | 604/74 |
| 6,705,920 B1 | * | 3/2004 | Engel | 450/36 |

* cited by examiner

*Primary Examiner*—Gloria M. Hale
(74) *Attorney, Agent, or Firm*—Olson & Hierl, Ltd.

(57) ABSTRACT

A breast stabilizing and positioning device comprises a torso band for enveloping and securement about the chest of a human female patient, a breast elevating module and a breast stabilizing ring. The torso band defines a through aperture sized to receive a human breast there through. The breast elevating module is attached to the torso band, and comprises a base framing the through aperture of the torso band and a plurality of flexible, elongate tabs extending radially from the base. The breast stabilizing ring is adapted for securement about the areolar region of a human breast and defines an opening sized to receive a human breast nipple there through. The breast stabilizing ring is adapted for removable engagement with the tabs of the breast elevating module. The present devices assist in performing diagnostic procedures such as ductal lavage, or a surgical procedure, such as removal of ducts from the breast nipple.

22 Claims, 5 Drawing Sheets

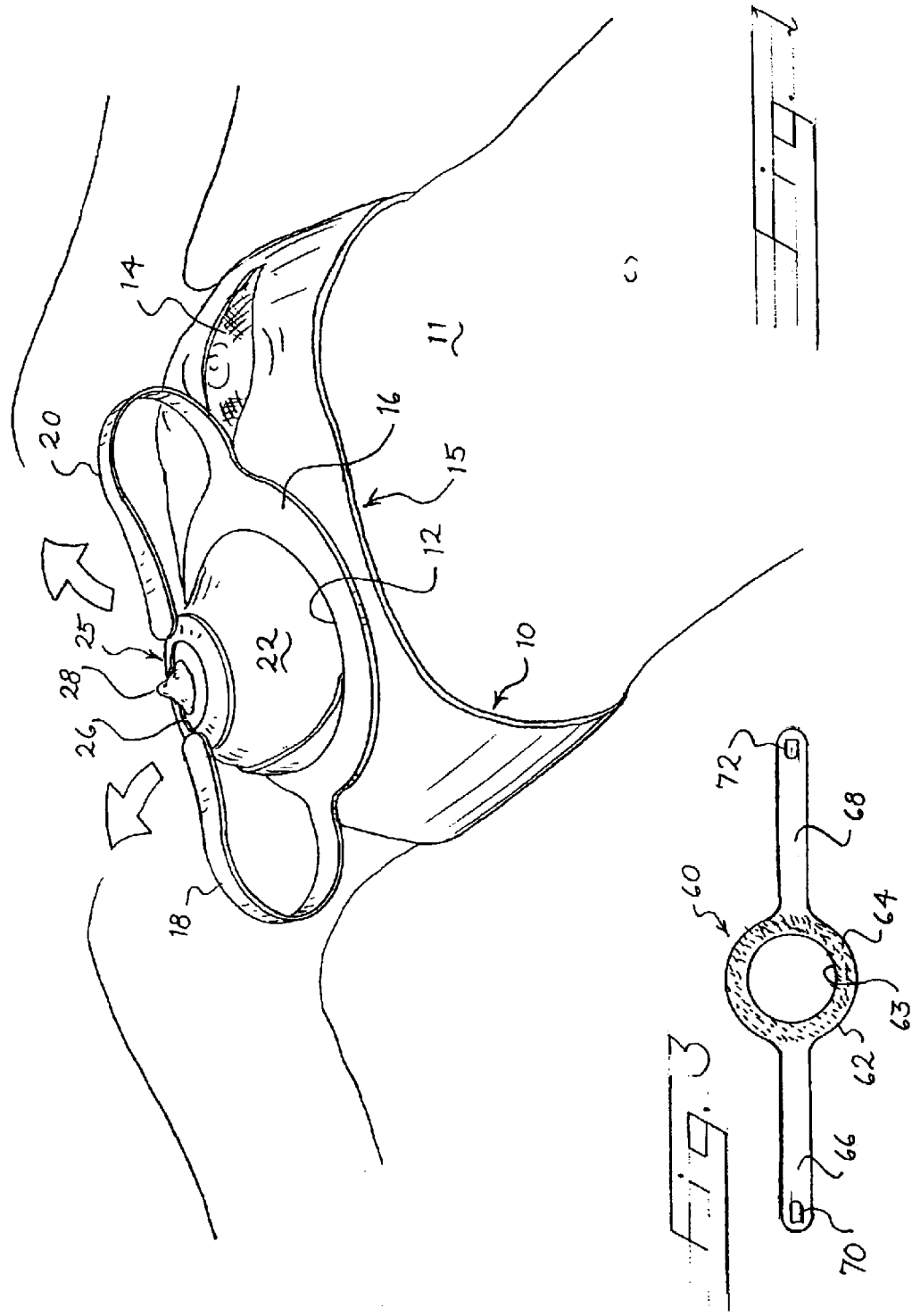

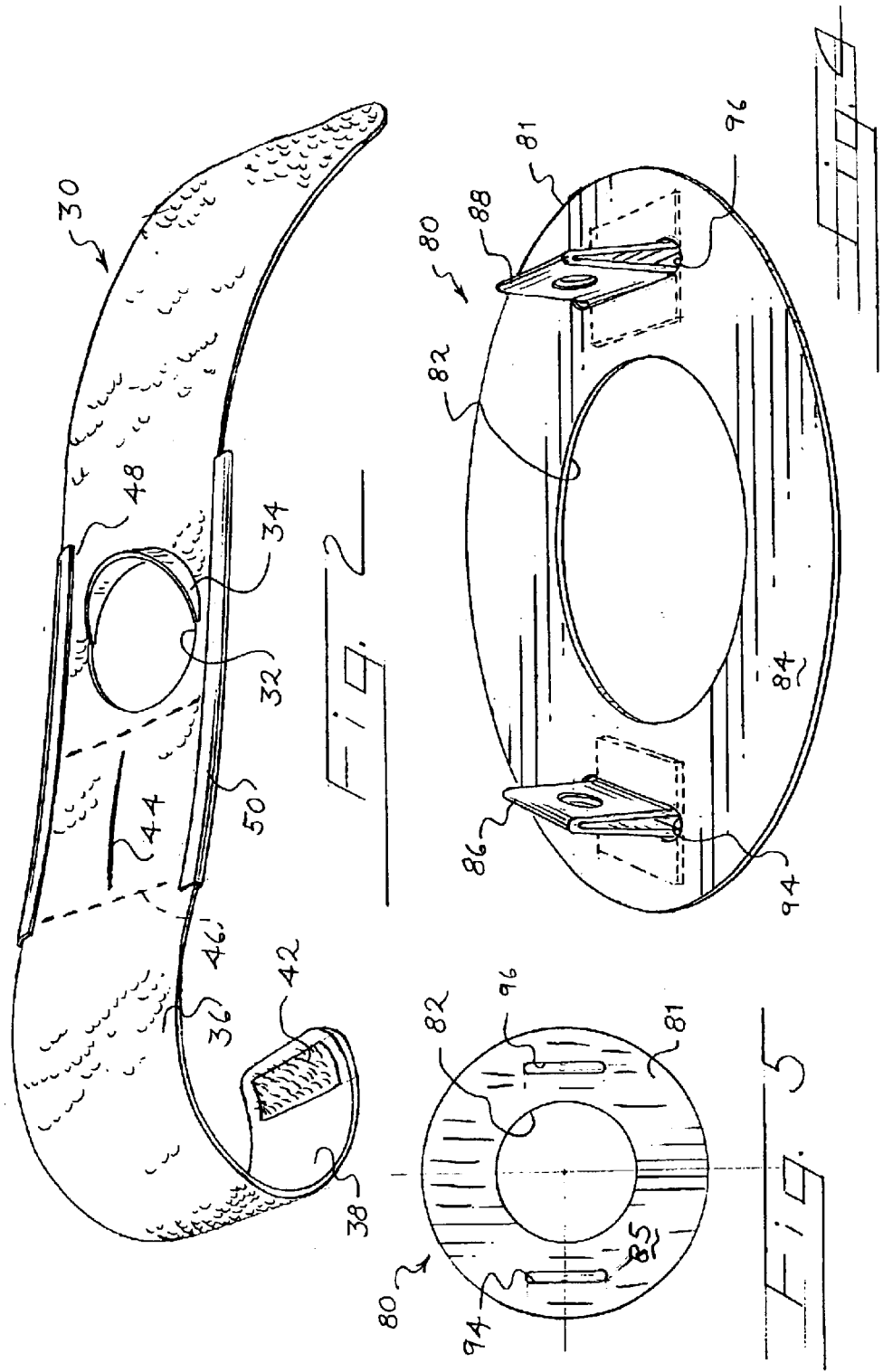

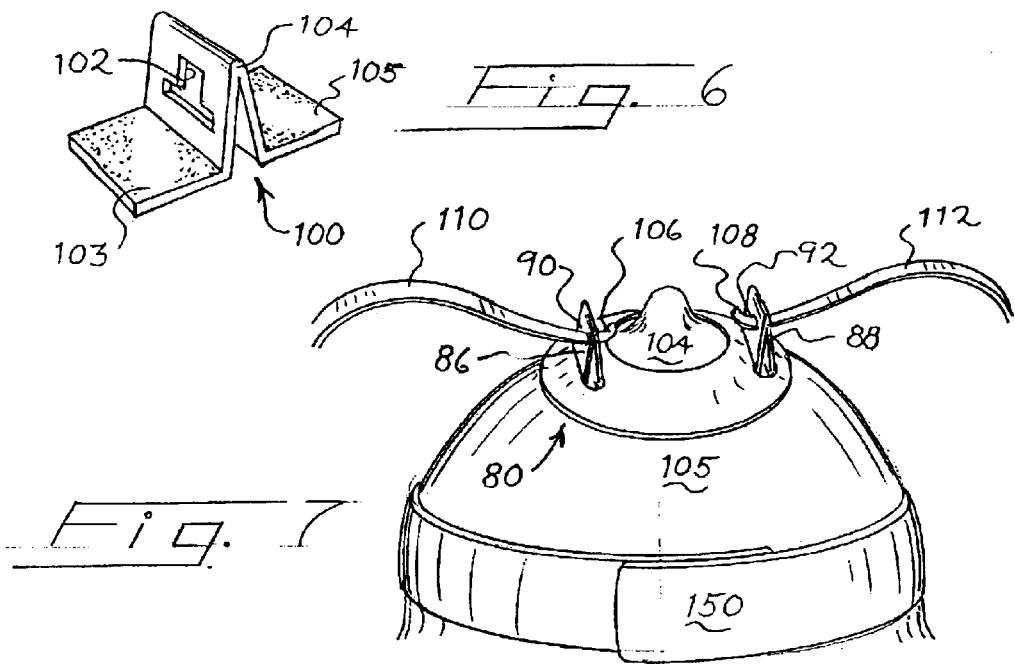
Fig. 6
Fig. 7
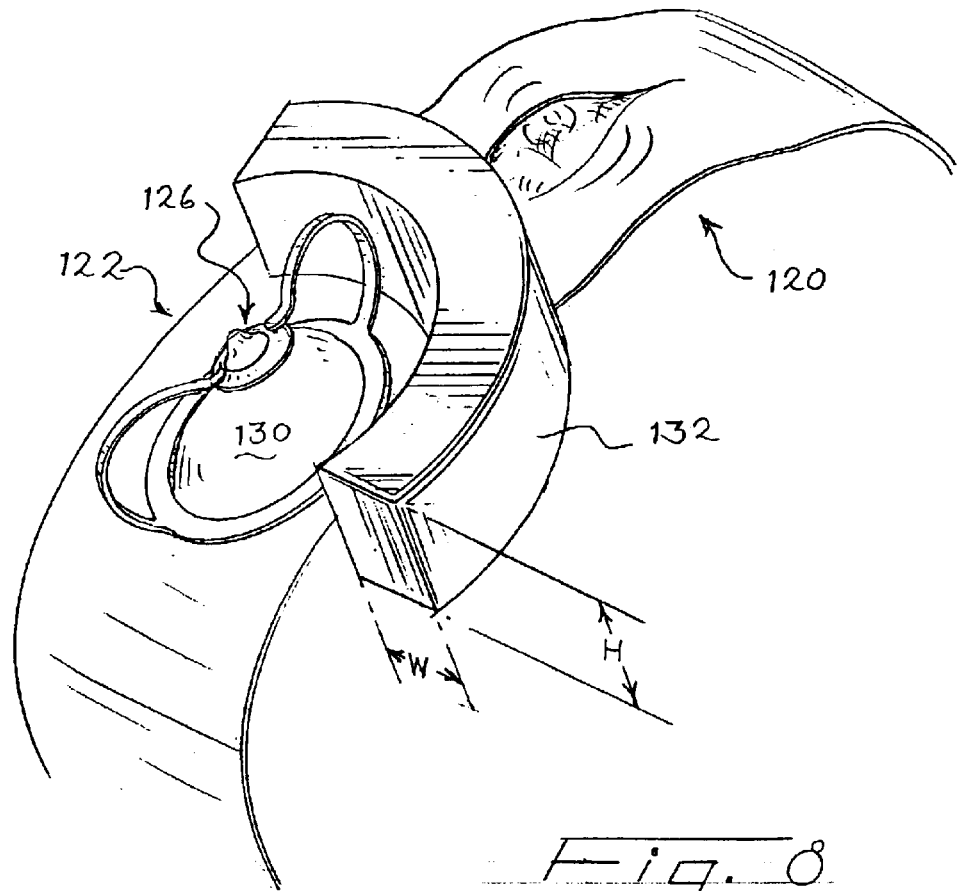
Fig. 8

BREAST STABILIZING AND POSITIONING DEVICE AND KIT

TECHNICAL FIELD OF THE INVENTION

This invention relates generally to devices and kits for use in clinical procedures performed on a human female breast. More specifically, the invention relates to devices and kits for stabilizing and positioning a human female breast during clinical diagnostic and surgical procedures on the breast.

BACKGROUND OF THE INVENTION

Breast cancer is one of the most common forms of cancer in women. A key to treatment is early detection. For example, annual mammograms have been recommended in hopes of early detection of breast cancer. One problem with mammographic imaging is that it can only detect breast cancer once it has taken tangible form as a tumor. All too often, breast cancer is discovered at a stage that is too far advanced, when therapeutic options and survival rates are severely limited. Therefore, more sensitive and reliable methods and devices are needed to detect cancerous, precancerous, and other cancer indicators of the breast at an early stage. Such methods and devices could significantly improve breast cancer survival. While breast cancer is most common among women, in rare instances breast cancer can occur in men.

A vast majority of breast cancers reportedly begin in the lining of mammary ducts. Studies have indicated that fluid within the mammary ducts can contain high levels of breast cancer markers, and that an estimated 80% to 90% of all breast cancers occur within the intraductal epithelium of the mammary glands. The fluid within the breast ducts contains an assemblage and concentration of hormones, growth factors and other potential markers comparable to those secreted by, or acting upon, the surrounding cells of the alveolar-ductal system. Mammary fluid also typically contains cells and solid cellular debris or products that can be used in cytological or immunological assays for breast cancer.

An early method of detecting breast cancer based on analysis of mammary fluid involves analyzing a sample of mammary fluid that was excreted by the mammary ducts without outside intervention. In other words, if a mammary duct is actively discharging a fluid, this fluid is analyzed. Often breasts do not discharge fluid spontaneously, even though breast cancer markers may be present in the mammary fluid.

One such diagnostic procedure based on the analysis of mammary fluid is ductal lavage. This method entails introducing saline into the mammary ducts via a small catheter and removing the introduced saline solution from the mammary ducts by vacuum. The recovered fluid is then subjected to immunological or cytological evaluation for the presence of breast cancer markers. This is a delicate procedure requiring considerable skill on the part of the clinician performing the catheterization. One advantage of such methods is that fluid samples can be retrieved from individual ducts, thus facilitating location of the cancerous area within the breast. One difficulty with such procedures is that they involve introduction of a catheter into the very small ducts in the breast nipple. Maintaining the breast in a suitable stable position during the catheterization and lavage procedure can be troublesome.

In situations where surgical intervention is required, for example to remove mammary ducts, maintaining the breast in a suitable stable position for the duration of the surgery is important. The breast can be manually held in position by a surgical assistant, for example with the aid of clamps and forceps. However, surgical procedures can be lengthy, and the assistant may be required to manually hold the breast in position for an extended period of time with attendant fatigue.

The present invention provides a device and kit for stabilizing and positioning a human breast for diagnostic or surgical procedures with minimal manual intervention to maintain the breast in a suitable position during the procedure.

SUMMARY OF THE INVENTION

A breast stabilizing and positioning device comprises a torso band, a breast elevating module and a breast stabilizing ring. The torso band is adapted for enveloping and securement about the chest of a human female patient and defines a through aperture sized to receive a human breast therethrough. The breast elevating module is attached to the torso band, and comprises a base framing the through aperture of the torso band and a plurality of flexible, elongate tabs that extend radially from the base. The breast stabilizing ring is adapted for securement about the areolar region of a human breast and defines an opening sized to receive a human breast nipple therethrough. The breast stabilizing ring is adapted for removable engagement with the tabs of the breast elevating module.

The breast elevating module includes at least two opposed elongate tabs extending from the base; however, there can be three or more spaced elongate tabs disposed radially around the base of the breast in any pattern that provides the desired degree of lift and support to the breast. Optionally, the length of the elongate tabs can be adjustable so that the degree of lifting force on the breast can be adjusted by the clinician.

In one embodiment, the breast stabilizing and positioning device is used to maintain a human breast in a position suitable for performing a clinical diagnostic procedure. The torso band is secured about the chest of a human female on which the procedure is to be performed. The breast subject to the procedure extends through the aperture, and the associated base of the breast elevating module frames the aperture. A breast stabilizing ring is secured about the areolar region of the breast by a physiologically tolerable, removable adhesive with the breast nipple extending through the opening defined therein. Each of the flexible, elongate tabs of the breast elevating module is engaged with the breast stabilizing ring to lift and hold the breast in a stable, extended position suitable for performing a clinical diagnostic procedure on the breast, such as a ductal lavage procedure, and the like.

The breast stabilizing and positioning device can also be used to maintain a human breast in a suitable stable position for performing a surgical procedure on the breast. The apertured torso band is secured about the chest of a human female patient with the breast on which the surgical procedure is to be performed extending through the aperture. The associated base of the breast elevating module that frames the aperture. The breast stabilizing ring can be secured about the areolar region of the breast by an adhesive, as described above. Alternatively, if blood flow from the surgical procedure is likely to interfere with the adhesive, the breast stabilizing ring can be secured to the breast by appropriate clamps. Each of the flexible, elongate tabs of the breast elevating module is engaged with the breast stabilizing ring to lift and hold the breast in a stable, extended position suitable for performing a surgical procedure on the breast, such as excision of the ductal system from the region of the breast nipple, and the like.

The present invention also encompasses kits containing at least one breast stabilizing and positioning device of the present invention, preferably in modular form.

BRIEF DESCRIPTION OF THE DRAWINGS

In the drawings,

FIG. 1 is a perspective view of a breast stabilizing and positioning device embodying the present invention as applied to a patient;

FIG. 2 is a perspective view of another breast stabilizing and positioning device embodying the present invention and provided with reinforcing bias tapes along opposite margins thereof;

FIG. 3 is a bottom plan view of a breast elevating module;

FIG. 4 is an enlarged perspective view of a breast stabilizing ring assembly;

FIG. 5 is a plan view of the breast stabilizing ring shown in FIG. 4;

FIG. 6 is a perspective view of a clip suitable for use with a breast stabilizing ring assembly shown in FIG. 4;

FIG. 7 is a perspective view of a breast stabilizing ring adhesively secured to a patient's breast and engaged by opposing tabs of a breast elevating module;

FIG. 8 is a perspective view of a breast stabilizing and positioning device embodying the present invention and provided with an optional hand rest;

DETAILED DESCRIPTION OF PREFERRED EMBODIMENTS

Figure 9:
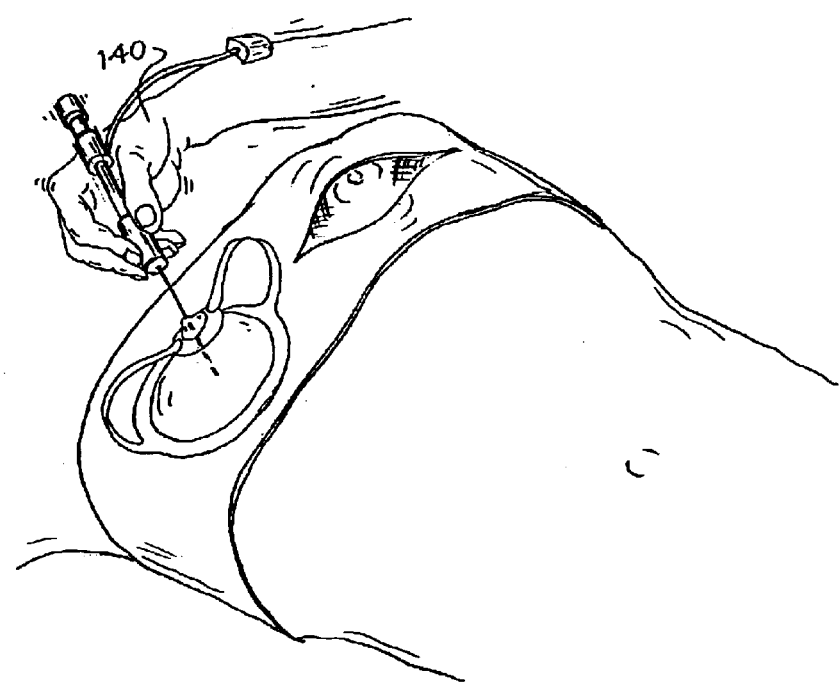
FIG. 9 is a perspective view illustrating the use of a breast stabilizing and positioning device of the present invention without a hand rest.

As used herein and in the appended claims, the term "breast nipple" and grammatical variations thereof refers to the entire areolar region of the breast including the areola and the protruding portion thereof commonly referred to as the "nipple."

A breast stabilizing and positioning device of the present invention comprises a torso band for enveloping and securement about the chest region of a human female patient, a breast elevating module, and a breast stabilizing ring. The torso band has an inner surface and an outer surface and defines a through aperture sized to receive a human breast therethrough. The breast elevating module is attachable to the torso band and comprises a base that frames the through aperture of the torso band and a plurality of flexible, elongate tabs, which extend radially from the base. The breast stabilizing ring has an inner surface that is adapted for securement about the areolar region of a human breast and an outer surface adapted to removably engage the tabs of the breast elevating module. The breast stabilizing ring defines an opening sized to receive a breast nipple therethrough.

The torso band preferably is made of a strip of fabric with complementary portions of a fastener at each end portion of the strip for securing the torso band around the chest of a patient. The fabric is preferably a stretchable fabric and includes a region of loops on its outer surface and a region of hooks permanently attached to the inner surface of one end portion of the torso band. The hooks and loops together form a hook and loop fastener for removably securing the torso band around the chest of the patient.

In a preferred embodiment, the torso band is constructed from a resilient composite fabric, such as a trilaminate fabric, which includes a liner layer, such as a nylon or polyester web, and the like; an elastomeric, foamed core layer, such as a neoprene foam, and the like; and an outer surface layer including a self-supporting web of entangled fibers suitable for engagement with the hook portion of a hook and loop fastener. Such preferred fabrics are commercially available and are commonly used in wet suit manufacture. A particularly preferred fabric is a stretchable trilaminate fabric having a neoprene foam core layer, a nylon or polyester liner layer and a surface layer comprising an unbroken loop (UBL) fabric that is suitable for engaging the hooks of a hook and loop fastener. Preferred fabrics are commercially available from RBX Industries, Inc., Roanoke, Va., under the trade name RUBATEX®, such as RUBATEX R-470-N having a 200 series UBL outer layer, and a nylon or polyester liner layer.

Alternatively, the torso band can be constructed of any convenient fabric, including, for example, cotton, acrylic, nylon, and the like, and the ends of the band can be fitted with complementary portions of at least one suitable faster, such as a hook and eye fastener, a hook and loop fastener, such as a VELCRO® brand hook and loop fastener, a snap button fastener, a side release plastic buckle, a center release plastic buckle, a ladder lock buckle, a press buckle, and the like.

The torso band can also include a breast support collar surrounding the through aperture, or a portion thereof. The collar provides extra support for the base of the breast. When present, the collar preferably surrounds a portion of the through aperture and extends outwardly away from and substantially normal to the outer surface of the torso band. The collar can be provided as a removable accessory, if desired.

The breast elevating module can be permanently attached or removably attachable to the torso band. The module preferably comprises a flexible plastic base ring having a plurality of elongate plastic tabs that extend radially away from the base ring. The distal end portions of the tabs are adapted to engage a complementary portion on the breast stabilizing ring. Preferably the distal end portions of the tabs include a hook or a catch, which is adapted to engage a complementary slot or clip on the breast stabilizing ring. The breast elevating module can be permanently attached to the torso band, framing the through aperture, for example, by gluing, stitching or riveting the base to the torso band. Preferably the breast elevating module is removably attachable to the torso band, such as with a hook and loop fastener, a plurality of snap fasteners, and the like. For example, a surface of the base can include hooks molded therein or attached thereto, which are adapted for engaging loops on the surface of the torso band surrounding the through aperture. The inner diameter of the base ring is selected to substantially match the diameter of the through aperture, so that the base ring frames the through aperture when secured to the torso band. The breast elevating device is preferably made of a flexible plastic such as polyethylene, polyvinyl chloride (PVC), polycarbonate, acrylic-butadiene-styrene copolymer (ABS), and the like.

The breast elevating module includes at least two opposed elongate tabs extending from the base. Alternatively, there can be three or more elongate tabs disposed radially around the base of the breast in any pattern that provides the desired degree of lift and support to the breast. For example, three tabs can be arranged at about 120 degree radial intervals around the base, or four tabs can be arranged at about 90 degree radial intervals around the base. In one embodiment, the point of attachment of the elongate tabs to the base of the breast elevating module can be adjustable so that the radial extent of the tabs away from the base, or the circumferential spacing of the tabs around the base, or both, can be adjusted by the clinician performing the clinical procedure on the breast.

The tabs of the breast elevating module are flexible enough to bend around about 180 degrees, i.e., toward the breast, and engage a breast stabilizing ring secured at the areolar region of the breast. The tabs act as leaf springs to lift the breast and support the breast in an elevated position when the patient is substantially supine. The degree of lift is dependent on the spring force of the bent tabs. Preferably the tabs are capable of providing a combined breast lifting force of up to about 5 pounds, so that the breast is pulled upward away from the torso when the patient is lying on her back. Optionally, the length of the elongate tabs can be adjustable so that the degree of lifting force on the breast can be adjusted by the clinician. For example, the tabs can comprise sliding or telescoping members that can be locked into a variety positions relative to each other to adjust the length. Alternatively, the tabs can be constructed for a plurality of removable, mutually engagable segments, the number of which segments are engaged determining the length of the tabs. A set of breast elevating modules having tabs of different flexibility can be utilized as well.

The breast stabilizing ring is sized to be positioned about the areolar region of a female human breast. The breast stabilizing ring is adapted to engage the distal end portions of the tabs of the breast elevating module. The breast stabilizing ring can include slots or clips for engaging the tabs of the breast elevating module.

When the present device is used to position and stabilize a breast for a diagnostic procedure, such as for a ductal lavage, the breast stabilizing ring is preferably secured to the breast by a physiologically tolerable, removable pressure sensitive adhesive. In a preferred embodiment, the breast stabilizing ring is an annular disk of adhesive backed surgical tape having clips attached thereto. The clips can be integral with the annular disk or removable, and are adapted to engage the distal end portions of the tabs of the breast elevating module. A preferred surgical tape is a 3M Medical Single-Coated Plastic Tape #1526, available from 3M Corporation, Minneapolis, Minn., which is a polyethylene film having a hypoallergenic adhesive coated on one side of the film and a printable liner on the other side of the film. The tape is about 0.005 inches thick and is suitable for gamma sterilization. The annular disk of adhesive tape defines an opening sized to fit a human breast nipple therethrough. Preferably, the surface of the annulus defines slots or holes through which clips can be inserted. The clips define apertures adapted to engage a interlocking distal end of a tab from the breast elevating module.

When the device is used to support a breast during a surgical procedure, especially where an adhesive may be undesirable or unable to adhere to the skin of the breast, the breast stabilizing ring can be attached to the breast with suitable clamps.

Optionally, the breast stabilizing and positioning devices of the present invention can include a removable hand rest; usually in the form of a foam or foam-filled pad or cushion, for use by the clinician to form a stable platform to rest the clinician's hand during a procedure. The pad can be curved or straight edged, and can extend to a height which is convenient perform a diagnostic procedure such as a ductal lavage procedure. Preferably the pad is taller than the height of the elevated breast upon which the procedure is being performed. The base of the pad can include the hook portion of a hook and loop fastener to removably secure the pad to the outer surface of the torso band. Typically the hand rest has a height in the range of about 4 to about 8 inches, a thickness in the range of about 2 to about 6 inches and a curved profile. The hand rest is positioned adjacent to a portion of the base of the breast elevating module, partially curving around the breast received in the through aperture of the torso band. Preferably the hand rest is made of a rigid or flexible foam material such as polystyrene foam, polyurethane, and the like.

Another aspect of the present invention is a packaged kit containing at least one breast stabilizing and positioning device of the present invention and instructional indicia. The device is preferable present in the kit in modular form and can be included in the packaging material in a disassembled or partially disassembled state. For example, the kit can include at least one torso band, at least one breast stabilizing module, separate from the band, and at least one breast stabilizing ring. Optionally, the kit can also include various accessories, such as a belt for wrapping and partially constricting the base of the breast to provide additional support to the breast, a hand rest for supporting a clinicians hand during a clinical procedure, a detachable collar for partially framing the through aperture of the torso band, and combinations thereof. Constriction of the base of the breast by support belt can also counteract breast nipple inversion, which occurs in some patients when in supine position with the breast elevated. In a preferred embodiment, a plurality of differently sized breast stabilizing modules and breast stabilizing rings can be provided in the same kit.

The instructional indicia can include a description of the device, instructions and schematics for assembling the device, instructions for using the device to stabilize and position a human breast for a clinical procedure, instructions for assembly, or any combination thereof. The instructional materials can be provided in the form of a label, a printed pamphlet, a video tape, a DVD, a CDROM, a DVDROM, or a combination thereof, and the like. Alternatively, the device can be provided in a fully assembled form.

Turning now to the Drawings, FIG. 1 illustrates a device of the present invention in use, with a human female breast stabilized and positioned therein. Torso band 10 is wrapped around the chest 11 of a sitting, reclining or supine female patient. Torso band 10 defines through aperture 12 and slot 14. Breast elevating module 15 includes base 16 framing through aperture 12 of torso band 10. The breast 22 of a patient is positioned in through aperture 12 of torso band 10 and extends through base 16 of breast elevating module 15. Flexible elongate tabs 18 and 20 are unitary with base 16, extend radially away from base 16 and curve inwardly toward and over breast 22. Distal end portion of tabs 18 and 20 are attached to breast stabilizing ring 25 which defines opening 26 and is positioned about nipple 28. Breast stabilizing ring 25 is adhesively attached to the surface of breast 22 with a pressure sensitive adhesive.

FIG. 2 is illustrates a preferred embodiment of the present invention. Torso band 30 defines through aperture 32 having a breast support collar 34 surrounding a portion of the through aperture 32. Breast support collar 34 is positioned towards the patient's feet when sitting and towards the arm when supine to counteract breast/gravity roll. Outer surface 36 of torso band 30 comprises a self-supporting web of entangled fibers suitable for engaging the hook portion of a hook and loop fastener. Inner surface 38 of torso band 30 comprises a lining of nylon or polyester fabric. A layer of neoprene foam rubber 40 is sandwiched between outer surface 36 and inner surface 38 of torso band 30. One end portion of torso band 30 includes a patch of hooks 42, attached to the inner surface 38 and adapted to engage loops of the web of entangled fibers covering outer surface 36. The hooks 42 and outer surface 36 together form a hook and loop fastener for securing the torso band around the chest of a female human patient. Torso band 30 also defines slot 44, which is covered by a stretchable fabric liner 46 attached to surface 38. Reinforcing bias tapes 48 and 50 are secured to the edges of torso band 30 in the region of through aperture 32 and slot 44.

FIG. 3 illustrates one embodiment of a breast elevating module 60. A base 62 in the form of an annular disk defines opening 63 and is provided with flexible hooks 64 on the bottom surface thereof. Two opposed, elongate tabs 66 and 68 extend radially away from base 62. Tabs 66 and 68 are flexible and can be readily bent about 180 degrees without permanent deformation or breakage. Catches 70 and 72 project from the bottom surfaces of distal end portions of tabs 66 and 68, respectively. Catches 70 and 72 are sized to be received in slots on a breast stabilizing ring (not shown), for removable securement of tabs 70 and 72 to a breast stabilizing ring such as ring 25 shown in FIG. 1.

FIGS. 4 and 5 illustrate a preferred embodiment of a breast stabilizing ring 80, which includes an annular disk 81 of surgical adhesive tape. Disk 81 defines opening 82 which is sized to receive a breast nipple therethrough. Annular disk 81 has a non-adhesive upper surface 84 and a lower surface 85 (FIG. 5) provided with a layer of surgical adhesive. Breast stabilizing ring 80 also includes two opposed clips 86 and 88, each defining a through hole 90 and 92, respectively, and adapted to engage the distal end portions of tabs from a breast elevating module (not shown). Clips 86 and 88 project away from upper surface 84 through slots 94 and 96, respectively, defined by annular disk 81. Clips 86 and 88 are adhesively secured to annular disk 81. FIG. 5 is a plan view of the lower surface 85 of annual disk 81, which usually has an outer diameter of about 3.5 inches (about 9 cm.), and an inner diameter of about 1.5 inches (about 3.8 cm.).

FIG. 6 illustrates an alternative clip 100 for use with annular disk 81. Clip 100 defines a T-shaped through slot 102 in upstanding portion 104 thereof and adapted for engaging a complementary latch hook on the distal end of a tab from a breast elevating module (not shown). Base panels 103 and 105 are adapted for adhesive attachment to lower surface 85 of disk 81.

FIG. 7 illustrates breast stabilizing ring 80 adhesively secured about a breast nipple 104 of breast 105, with through holes 90 and 92 of clips 86 and 88 receiving the distal end portions 106 and 108 of tabs 110 and 112, respectively from a breast elevating module. For relatively large breasts an optional breast band or belt 150 circumscribing the breast below ring 80 can provide further stabilization.

FIG. 8 illustrates breast stabilizing and positioning device 120, comprising torso band 122, breast elevating module 124 and breast stabilizing ring 126, all positioned for use about breast 130. A hand rest such as pad 132 is secured to torso band 122 and partially frames breast 130 as well as breast elevating module 124. Pad 132 is in the form of a partial annular segment of hollow cylinder, having a height H of about 6 inches (about 15.4 cm.) and a segmental width W of about 3 inches (about 7.7 cm.). The segment defines an arc of about 120 degrees.

Figure 10:
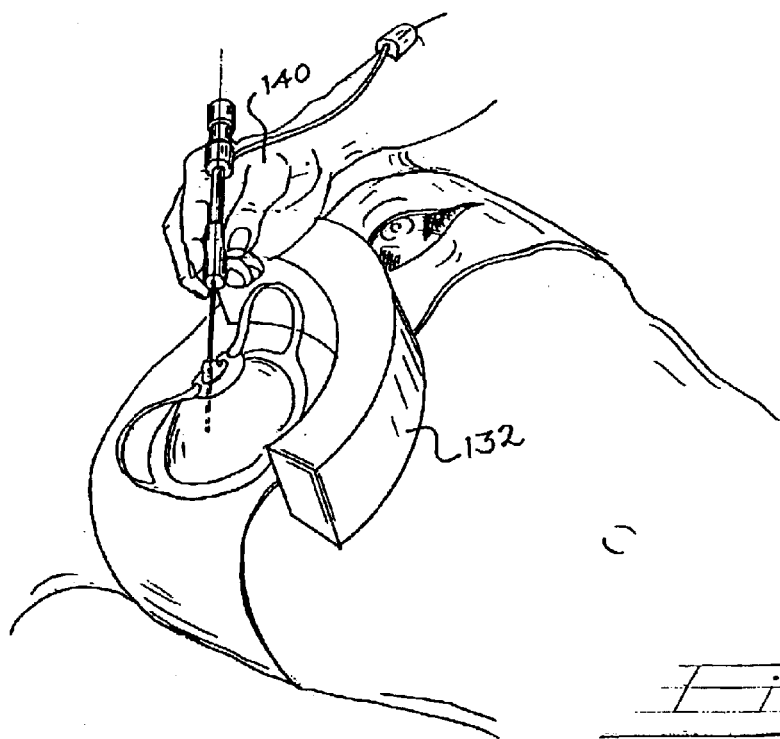
FIG. 10 is a perspective view illustrating the use of a breast stabilizing and positioning device of the present invention equipped with a hand rest.

FIGS. 9 and 10 illustrate device 120 of FIG. 8 in use by a clinician performing a ductal lavage procedure, with (FIG. 10) and without (FIG. 9) hand rest pad 132. The hand 140 of the clinician is supported by pad 132 and provides stability as well as ergonomic benefits during the clinical procedure.

Figure 11:
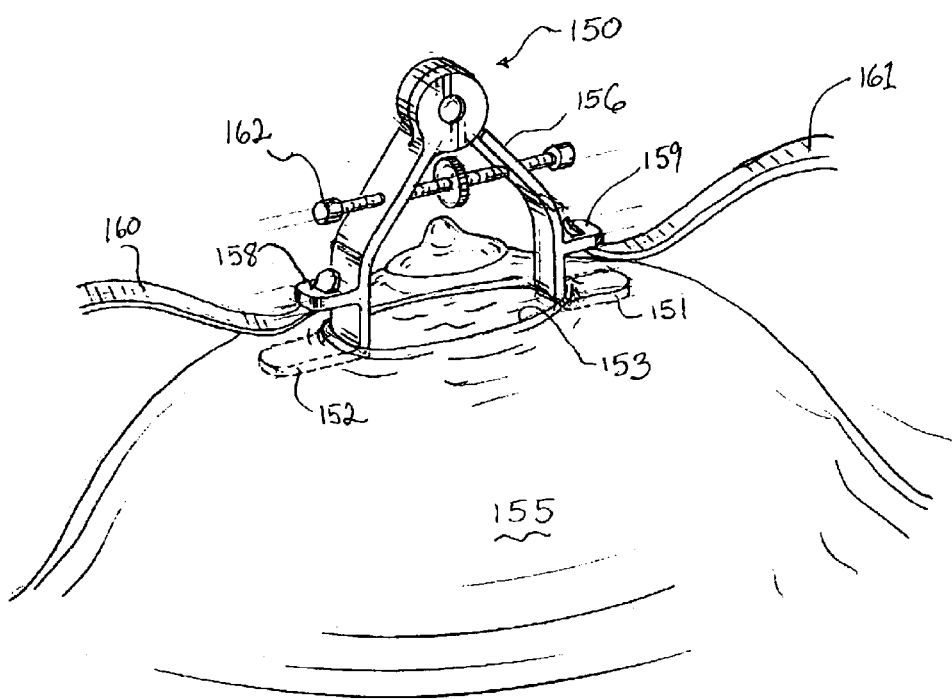
FIG. 11 illustrates an embodiment of the breast stabilizing and positioning device of the present invention where the breast stabilizing ring is replaced with an adjustable ductotomy surgical retractor, for use in breast surgery applications.

FIG. 11 illustrates an embodiment of the breast stabilizing and positioning device of the present invention where the breast stabilizing ring is replaced with an adjustable ductotomy surgical retractor. This embodiment of the present invention is useful in breast surgery, such as removal of the mammary ducts (i.e., breast ductotomy), where adhesive attachment of a breast stabilizing ring is impractical due to bleeding. In FIG. 11, adjustable retractor 150 having flattened foot portions 151 and 152, is positioned within a 2–3 cm incision 153 in breast 155. Incision 153 is made at the areola margin and foot portions 151 and 152 of retractor 150 are passed through incision 153 to elevate the breast from within. An upper portion 156 of retractor 150 defines loops 158 and 159 for removable attachment to tabs 160 and 161 of a breast elevating module of the invention as described above. A user adjustable positioner, such as screw 162 is provided on refractor 150 to adjust the distance between foot portions 151 and 152 of retractor 150, as needed, to fit within incision 153. In this embodiment, tabs 160 and 161 provide a lifting force on retractor 150, which in turn lifts the breast 155.

The foregoing description is to be taken as illustrative, but not limiting. Still other variants within the spirit and scope of the present invention will readily present themselves to those skilled in the art.

We claim:

1. A breast stabilizing and positioning device comprising:
    a torso band for enveloping and securement about the chest of a human female patient, the torso band having an outer surface and an inner surface and defining a through aperture sized to receive a human breast therethrough;
    a breast elevating module attached to the torso band, and having an annular base framing the through aperture of the torso band and a plurality of flexible, elongate tabs extending radially away from the base, each tab having a distal end portion; and
    a breast stabilizing ring having an upper surface and an lower surface and defining an opening sized to receive a breast nipple therethrough, the lower surface of the breast stabilizing ring being adapted for securement about the areolar region of a human breast, and the upper surface of the ring being adapted to removably engage the distal end portions of the tabs of the breast elevating module.

2. The device of claim 1 wherein the outer surface of the torso band comprises a self-supporting web of entangled fibers suitable for engaging a region of the inner surface of the torso band having plurality of hooks for securing the band around the chest of a patient.

3. The device of claim 1 wherein the torso band comprises a laminated fabric having a nylon or polyester inner surface layer, a foamed neoprene core layer, and an outer surface layer comprising a self-supporting web of entangled fibers suitable for engaging the hook portion of a hook and loop fastener.

4. The device of claim 1 wherein the torso band defines at least one elongate slit spaced from the through aperture.

5. The device of claim 4 wherein the inner surface of the torso band includes an elastic liner covering the slit.

6. The device of claim 1 wherein the torso band includes a breast support collar partially surrounding the through aperture and projecting away from the outer surface of the torso band.

7. The device of claim 6 wherein the breast support collar is detachable.

8. The device of claim 6 wherein the collar includes a self-supporting web of entangled fibers suitable for engaging the hook portion of a hook and loop fastener.

9. The device of claim 2 wherein the base of the breast elevating module includes hooks capable of removably engaging the outer surface of the torso band to secure the breast elevating module around the through aperture of the torso band.

10. The device of claim 1 wherein the tabs of the breast elevating module act as leaf springs capable of providing a combined breast lifting force of at least about 5 pounds.

11. The device of claim 1 wherein the tabs of the breast elevating module have an adjustable length.

12. The device of claim 1 wherein the tabs have an adjustable length.

13. The device of claim 1 having a pair of opposed, flexible, elongate tabs extending from the base of the breast elevating module.

14. The device of claim 1 wherein the outer surface of the breast stabilizing ring includes a plurality of slots for engaging the distal ends of the tabs of the breast elevating device.

15. The device of claim 1 wherein the breast stabilizing ring includes a plurality of detachable clips adapted to engage distal end portions of the tabs of the breast elevating module.

16. The device of claim 1 wherein the inner surface of the breast stabilizing ring bears a physiologically tolerable adhesive.

17. A kit comprising packaging material containing at least one breast stabilizing and positioning device, and comprising:
   a torso band for enveloping and securement about the chest of a human female patient, the torso band defining a through aperture sized to receive a human breast therethrough;
   a breast elevating module attachable to the torso band and having a base in the form of an annular disk capable of framing the through aperture of the torso band and a plurality of flexible, elongate tabs extending radially away from the base, each tab having a distal end portion; and
   a breast stabilizing ring having an inner surface and an outer surface, and defining an opening sized to receive a breast nipple therethrough, the inner surface of the breast stabilizing ring being adapted for securement about the areolar region of a human breast, and the outer surface of the ring being adapted to removably engage the distal end portions of the tabs of the breast elevating module.

18. The kit of claim 17 wherein the breast stabilizing and positioning device is modular and is present in the packaging material in a disassembled or partially disassembled state.

19. The kit of claim 17 wherein the kit includes a plurality of breast stabilizing rings.

20. The kit of claim 17 wherein the kit includes a plurality of breast elevating modules.

21. The kit of claim 17 wherein the kit further includes an accessory selected from the group consisting of a breast belt for securement about the human female breast to constrict the breast while the breast is engaged in the breast stabilizing and positioning device, a detachable hand rest for supporting the hand of a clinician performing a clinical procedure on a patient's breast, a detachable breast support collar for partially framing the through aperture of the torso band to provide added support for a breast received therethrough, and a combination thereof.

22. A breast stabilizing and positioning device comprising:
   a torso band for enveloping and securement about the chest of a human female patient, the torso band having an outer surface and an inner surface and defining a through aperture sized to receive a human breast therethrough;
   a breast elevating module attached to the torso band, and having an annular base framing the through aperture of the torso band and a plurality of flexible, elongate tabs extending radially away from the base, each tab having a distal end portion; and
   an adjustable ductotomy surgical retractor having an upper portion and two flattened foot portions sized to pass through a 2–5 cm ductectomy incision at the margin of the areola of the breast, the foot portions of the retractor being adapted for lifting breast mass under the areolar region of a human breast, and the upper portion of the retractor being adapted to removably engage the distal end portions of the tabs of the breast elevating module.

* * * * *